(12) United States Patent
Zielinski et al.

(10) Patent No.: US 9,488,564 B2
(45) Date of Patent: *Nov. 8, 2016

(54) METHODS AND APPARATUSES FOR DETECTING MOISTURE

(71) Applicant: Revive Electronics, LLC, Fishers, IN (US)

(72) Inventors: Reuben Quincey Zielinski, Fishers, IN (US); Joel Christopher Trusty, Fishers, IN (US); Micah Neil Trusty, Indianapolis, IN (US)

(73) Assignee: Revive Electronics, LLC, Carmel, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/080,595

(22) Filed: Nov. 14, 2013

(65) Prior Publication Data

US 2014/0130573 A1    May 15, 2014

Related U.S. Application Data

(60) Provisional application No. 61/726,151, filed on Nov. 14, 2012.

(51) Int. Cl.
*G01N 19/10* (2006.01)
*G01N 27/04* (2006.01)
*G01N 1/24* (2006.01)

(52) U.S. Cl.
CPC ............ *G01N 19/10* (2013.01); *G01N 27/048* (2013.01); *G01N 1/24* (2013.01)

(58) Field of Classification Search
CPC ............ G01N 7/00; G01N 7/10; G01N 7/14; G01N 7/02; G01N 25/56; G01N 25/60; G01N 25/68; G01N 27/121; G01N 27/225; G01N 27/048; G01N 27/223; G01N 27/605; G01N 31/222; G01N 33/0009; G01N 33/0011; G01N 33/0031; G01N 33/0016; G01N 19/10; G01N 1/24; G05D 22/00
USPC ....... 73/23.2, 29.01, 29.03, 29.04, 29.05, 73
See application file for complete search history.

(56) References Cited

U.S. PATENT DOCUMENTS 2,496,054 A    1/1950    Hoyler
2,846,710 A    8/1958    Haka
(Continued)

FOREIGN PATENT DOCUMENTS

CN    2065321    11/1990
CN    2065321MT    11/1990
(Continued)

OTHER PUBLICATIONS

Lori MacVittie, Remote Management In-Reach, Aug. 21, 2003, Network Computing, 14, 16; ProQuest p. 22.*
(Continued)

*Primary Examiner* — Hezron E Williams
*Assistant Examiner* — Marrit Eyassu
(74) *Attorney, Agent, or Firm* — Baker & McKenzie LLP

(57) ABSTRACT

Methods and apparatuses for detecting moisture are disclosed. Embodiments detect the existence and/or level of moisture in electronic devices, such as by using one or more moisture sensors that removably connect to a pre-existing port in the electronic device (such as a headphone jack or similar port). Some embodiments detect a component of the ambient air (such as moisture level) to improve the accuracy of the moisture detector. Some embodiments decrease pressure at the port using a pneumatic pump and move gas from the electronic device into the moisture detector. Some embodiments detect the movement of air in the vicinity of at least one moisture sensor (such as by measuring pressure) and use this information to improve the accuracy of the moisture detector. Some embodiments display information related to the moisture in the electronic device and/or the ambient air.

24 Claims, 11 Drawing Sheets

(56) References Cited

U.S. PATENT DOCUMENTS

| | | | |
|---|---|---|---|
| 3,897,604 | A | 8/1975 | Weimer |
| 3,932,944 | A | 1/1976 | Chiba |
| 4,020,563 | A | 5/1977 | Hoefer |
| 4,386,471 | A | 6/1983 | Bowrey et al. |
| 4,515,751 | A * | 5/1985 | Krieg, Jr. .................. 422/86 |
| 4,589,971 | A | 5/1986 | Mayeaux |
| 4,704,805 | A | 11/1987 | Kaya et al. |
| 4,733,428 | A | 3/1988 | Malinge et al. |
| 4,882,851 | A | 11/1989 | Wennerstrum et al. |
| 5,005,410 | A | 4/1991 | Webster et al. |
| 5,067,251 | A | 11/1991 | Zlobinsky et al. |
| 5,293,697 | A | 3/1994 | Kawakami |
| 5,318,164 | A | 6/1994 | Barnes et al. |
| 5,335,703 | A | 8/1994 | deJong |
| 5,343,747 | A | 9/1994 | Rosen |
| 5,349,845 | A | 9/1994 | Blom |
| 5,456,025 | A | 10/1995 | Joiner et al. |
| 5,578,753 | A * | 11/1996 | Weiss et al. .............. 73/335.02 |
| 5,625,962 | A | 5/1997 | Fleissner |
| 5,671,546 | A | 9/1997 | Haala |
| 5,852,879 | A | 12/1998 | Schumaier |
| 5,889,466 | A | 3/1999 | Ferguson |
| 5,992,049 | A | 11/1999 | Trost |
| 6,025,580 | A | 2/2000 | Yagi |
| 6,039,696 | A | 3/2000 | Bell |
| 6,122,836 | A | 9/2000 | Tenedini et al. |
| 6,399,920 | B1 | 6/2002 | Guinn |
| 6,551,552 | B1 | 4/2003 | Lyublinski et al. |
| 6,557,268 | B1 | 5/2003 | Berg et al. |
| 6,568,249 | B2 | 5/2003 | Devine |
| 6,622,399 | B1 | 9/2003 | Theriault et al. |
| 6,675,636 | B2 | 1/2004 | Sadler |
| 6,821,025 | B2 | 11/2004 | Gerhard |
| 6,834,443 | B2 | 12/2004 | Bloemendaal |
| 6,893,530 | B2 | 5/2005 | Kishimoto et al. |
| 6,938,359 | B2 | 9/2005 | Birgersson et al. |
| 7,050,837 | B2 | 5/2006 | Menz et al. |
| 7,194,822 | B2 | 3/2007 | Kolari |
| 7,205,900 | B2 | 4/2007 | Liu et al. |
| 7,243,857 | B2 | 7/2007 | Kallestad |
| 7,460,350 | B2 | 12/2008 | Talbot et al. |
| 7,557,466 | B2 | 7/2009 | Wong et al. |
| 7,594,343 | B2 | 9/2009 | Woerdehoff et al. |
| 7,612,315 | B2 | 11/2009 | Corradini |
| 7,631,538 | B2 | 12/2009 | Imhof |
| 7,665,226 | B2 | 2/2010 | Tsuruta et al. |
| 7,814,678 | B2 | 10/2010 | Romanek |
| 8,058,588 | B2 | 11/2011 | Gagas et al. |
| 8,108,074 | B2 | 1/2012 | Boder |
| 8,112,900 | B2 | 2/2012 | Romanek |
| 8,203,689 | B2 | 6/2012 | Gomi |
| 8,281,499 | B2 | 10/2012 | Friesen et al. |
| 8,355,233 | B2 | 1/2013 | Schumacher et al. |
| 8,416,542 | B2 | 4/2013 | Nakamura |
| 8,446,049 | B2 | 5/2013 | Lee |
| 8,498,087 | B2 | 7/2013 | Rabu et al. |
| 8,886,971 | B2 * | 11/2014 | Chuang .................. 713/300 |
| 2001/0045421 | A1 * | 11/2001 | Sullivan .................. 219/209 |
| 2003/0019124 | A1 | 1/2003 | Miyakawa et al. |
| 2003/0115768 | A1 | 6/2003 | Hoffman |
| 2004/0050076 | A1 * | 3/2004 | Palfy et al. ................. 62/155 |
| 2004/0079136 | A1 * | 4/2004 | Pillion .................. 73/23.2 |
| 2005/0079888 | A1 | 4/2005 | Menz et al. |
| 2005/0218239 | A1 | 10/2005 | Busch |
| 2006/0058069 | A1 | 3/2006 | Garcia et al. |
| 2006/0208914 | A1 * | 9/2006 | Liu et al. .................. 340/620 |
| 2006/0255166 | A1 | 11/2006 | Imamura et al. |
| 2007/0258870 | A1 * | 11/2007 | Brown et al. ............ 422/186.07 |
| 2008/0204218 | A1 * | 8/2008 | Tupman ............... G11B 27/36 340/501 |
| 2008/0281528 | A1 * | 11/2008 | Relle, Jr. .................. 702/19 |
| 2009/0019718 | A1 | 1/2009 | Mittleman et al. |
| 2009/0145783 | A1 | 6/2009 | Forker |
| 2009/0158614 | A1 | 6/2009 | Singh et al. |
| 2009/0272176 | A1 * | 11/2009 | Lopez et al. .................. 73/29.01 |
| 2009/0273480 | A1 * | 11/2009 | Mittleman et al. ........... 340/604 |
| 2010/0095504 | A1 | 4/2010 | Slack et al. |
| 2010/0103566 | A1 * | 4/2010 | Chen .................. 361/1 |
| 2010/0122470 | A1 | 5/2010 | Davis et al. |
| 2010/0304091 | A1 * | 12/2010 | Wang .................. 428/172 |
| 2011/0047814 | A1 | 3/2011 | Watson et al. |
| 2011/0067262 | A1 | 3/2011 | Eero |
| 2011/0099831 | A1 | 5/2011 | Parisi et al. |
| 2011/0137607 | A1 * | 6/2011 | Hsieh .................. 702/130 |
| 2012/0020015 | A1 | 1/2012 | Tian et al. |
| 2012/0038374 | A1 * | 2/2012 | Johnson .................. 324/694 |
| 2012/0085324 | A1 | 4/2012 | Saito et al. |
| 2012/0171462 | A1 | 7/2012 | Tsai |
| 2012/0304483 | A1 | 12/2012 | Sirard et al. |
| 2013/0088094 | A1 | 4/2013 | Paik |
| 2013/0096375 | A1 * | 4/2013 | Iyama et al. .................. 600/103 |
| 2013/0111227 | A1 | 5/2013 | Sauerwein, Jr. |
| 2013/0167874 | A1 | 7/2013 | Mittleman et al. |
| 2013/0182360 | A1 | 7/2013 | Stevens et al. |

FOREIGN PATENT DOCUMENTS

| | | |
|---|---|---|
| CN | 2065321 U | 11/1990 |
| CN | 201018665 | 2/2008 |
| CN | 101986360 | 3/2011 |
| CN | 201955259 | 8/2011 |
| CN | 201955259 U | 8/2011 |
| EP | 0539607 | 5/1993 |
| EP | 1125177 | 1/2004 |
| JP | 2001197175 | 7/2001 |
| JP | 2001197175 A | 7/2001 |
| JP | 2011171894 | 9/2011 |
| WO | 0023861 | 4/2000 |
| WO | 0053983 | 9/2000 |
| WO | 2007033493 | 3/2007 |
| WO | 2009087102 | 7/2009 |
| WO | 2010070551 | 6/2010 |

OTHER PUBLICATIONS

International Search Report and Written Opinion issued in PCT/US2013/070178 dated Feb. 24, 2014.

International Search Report and Written Opinion issued in PCT/US2013/024277, pp. 1-16 May 5, 2013.

"How to Dry Out a Wet Cell Phone," ehow.com, http://www.ehow.com/print/how__2042819_dry-out-wet-cell-phone.html, pp. 1-2. Jun. 5, 2013.

U.S. Trademark Registration No. 4,280,438 for the mark DRYBOX Jan. 22, 2013.

Exhibitor News from International CTIA Wireless 2012 May 3, 2013.

Lucio, Valentino, "A Solution for Soaked Cells," San Antonio Express-News, pp. 1-3 Oct. 19, 2011.

Cooper, Sean, "Drybox Rescue Station: the ultimate cellphone drying system (hands-on)," www.engadget.com, pp. 1-13 May 22, 2013.

DRYBOX The New Way to Save a Wet Phone Fast, http://www.dryboxrescue.com/, pp. 1-5 Jun. 26, 2013.

International Preliminary Report on Patentability issued in PCT/US2013/024277, pp. 1-12 Aug. 8, 2014.

Non-Final Rejection issued in U.S. Appl. No. 13/756,879. Sep. 20, 2013.

Response After Non-Final Action filed in U.S. Appl. No. 13/756,879. Dec. 20, 2013.

Final Rejection issued in U.S. Appl. No. 13/756,879. Feb. 28, 2014.

Response After Final Action filed in U.S. Appl. No. 13/756,879. May 28, 2014.

Response After Final Action filed in U.S. Appl. No. 13/756,879. Jun. 13, 2014.

Advisory Action issued in U.S. Appl. No. 13/756,879. Jun. 18, 2014.

(56) References Cited

OTHER PUBLICATIONS

Advisory Action issued in U.S. Appl. No. 13/756,879. Jul. 9, 2014.
Request for Continued Examination filed in U.S. Appl. No. 13/756,879. Aug. 28, 2014.
International Search Report and Written Opinion issued in PCT/US2014/028634. Aug. 27, 2014.
Non-Final Rejection issued in U.S. Appl. No. 13/756,879. Sep. 20, 2014.
Response After Non-Final Action filed in U.S. Appl. No. 13/756,879. Dec. 29, 2014.
Notice of Allowance issued in U.S. Appl. No. 13/756,879. Jan. 20, 2015.

* cited by examiner

FIG. 6 TEST MODE

FIG. 10 CALIBRATION MODE

METHODS AND APPARATUSES FOR DETECTING MOISTURE

This application claims the benefit of U.S. Provisional Application No. 61/726,151, filed Nov. 14, 2012, the entirety of which is hereby incorporated herein by reference.

FIELD

Embodiments of the present disclosure generally relate to detecting, and to detecting moisture in an electronic device, such as portable electronic devices.

BACKGROUND

Electronic devices are frequently manufactured using ultra-precision parts for tight fit-and-finish dimensions that are intended to keep moisture from entering the interior of the device. These electronic devices frequently have miniaturized solid-state transistorized memory for capturing and storing digitized media in the form of phone contact lists, e-mail addresses, digitized photographs, digitized music and the like. Many electronic devices are also manufactured to render disassembly by owners and or users difficult without rendering the device inoperable, even prior to drying attempts. With the continued miniaturization of electronics and increasingly powerful computerized software applications, it is commonplace for people today to carry multiple portable electronic devices. Cell phones are currently more ubiquitous than telephone land lines, and many people, on a daily basis throughout the world, inadvertently subject these devices to unintended contact with water. This occurs daily in the bathroom, kitchen, swimming pools, lakes, washing machines, or any other areas where various electronic devices can likely be submerged in water or subject to high-humid conditions.

SUMMARY

In the conventional art, difficulties currently exist in determining the level of moisture within an electronic device. Electronic device manufacturers commonly add "liquid contact indicators" (LCIs) to portable electronic devices to indicate when a device has been exposed to moisture; however, these devices merely indicate whether the device has been exposed to moisture levels that exceed the pre-set conditions of the LCI, and fail to detect the severity of the moisture levels. The advent of newer, more sophisticated and reliable methods of drying portable electronic devices are rendering LCI's useless. Moreover, if a user can defeat the LCI visual indicator, then the repair or retail shop will not know whether the portable device is truly damaged from water, or whether the user has a valid warranty claim. Thus, a new type of moisture level detecting and indicating system is needed to allow individuals and repair shops to sample and determine the level of moisture within a portable electronic device without the need for disassembly.

Embodiments of the present disclosure provide methods and apparatuses for the detection of water in portable electronic devices, such as cell phones, digital music players, pagers, cameras, tablet computers and the like. This may be useful in instances where the electronic devices have been subjected to liquid water, high-humidity conditions, or other unintended deleterious wetting agents that could render such devices inoperable.

In some embodiments the moisture detection is automatic after the moisture detector has been operatively connected to the electronic device.

In alternate embodiments, the moisture detection can be performed without any disassembly of the electronic device.

At least one embodiment includes a user-controlled vacuum plenum that scavenges air from within the portable electronic device to determine the level of water or moisture within the device.

Further embodiments include a user-controlled vacuum plenum that simultaneously scavenges air from within the portable electronic device while sampling the relative humidity outside the device, which may be used to improve the accuracy of the amount of moisture detected. The sampling and measuring of the relative humidity within the device may be controlled by a microprocessor (also referred to as a microcontroller), and may be displayed on a user interface to allow users (such as those in electronics repair and retail shops) to quickly determine whether the portable electronic device contains water or moisture within its enclosed interior.

Certain preferred features of the present disclosure address these and other needs and provide other important advantages. Embodiments of the present disclosure relate to equipment and methods for the vacuum scavenging of air from within the interior of a portable electronic device. More particularly, certain embodiments of the disclosure relate to an automatic vacuum that pulls entrapped air across a moisture sensor to determine the level of moisture within the electronics package.

This summary is provided to introduce a selection of the concepts that are described in further detail in the detailed description and drawings contained herein. This summary is not intended to identify any primary or essential features of the claimed subject matter. Some or all of the described features may be present in the corresponding independent or dependent claims, but should not be construed to be a limitation unless expressly recited in a particular claim. Each embodiment described herein is not necessarily intended to address every object described herein, and each embodiment does not necessarily include each feature described. Other forms, embodiments, objects, advantages, benefits, features, and aspects of the present disclosure will become apparent to one of skill in the art from the detailed description and drawings contained herein. Moreover, the various apparatuses and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

Some of the figures shown herein may include dimensions or may have been created from scaled drawings. However, such dimensions, or the relative scaling within a figure, are by way of example, and not to be construed as limiting.

DETAILED DESCRIPTION OF THE ILLUSTRATED EMBODIMENTS

Figure 1:
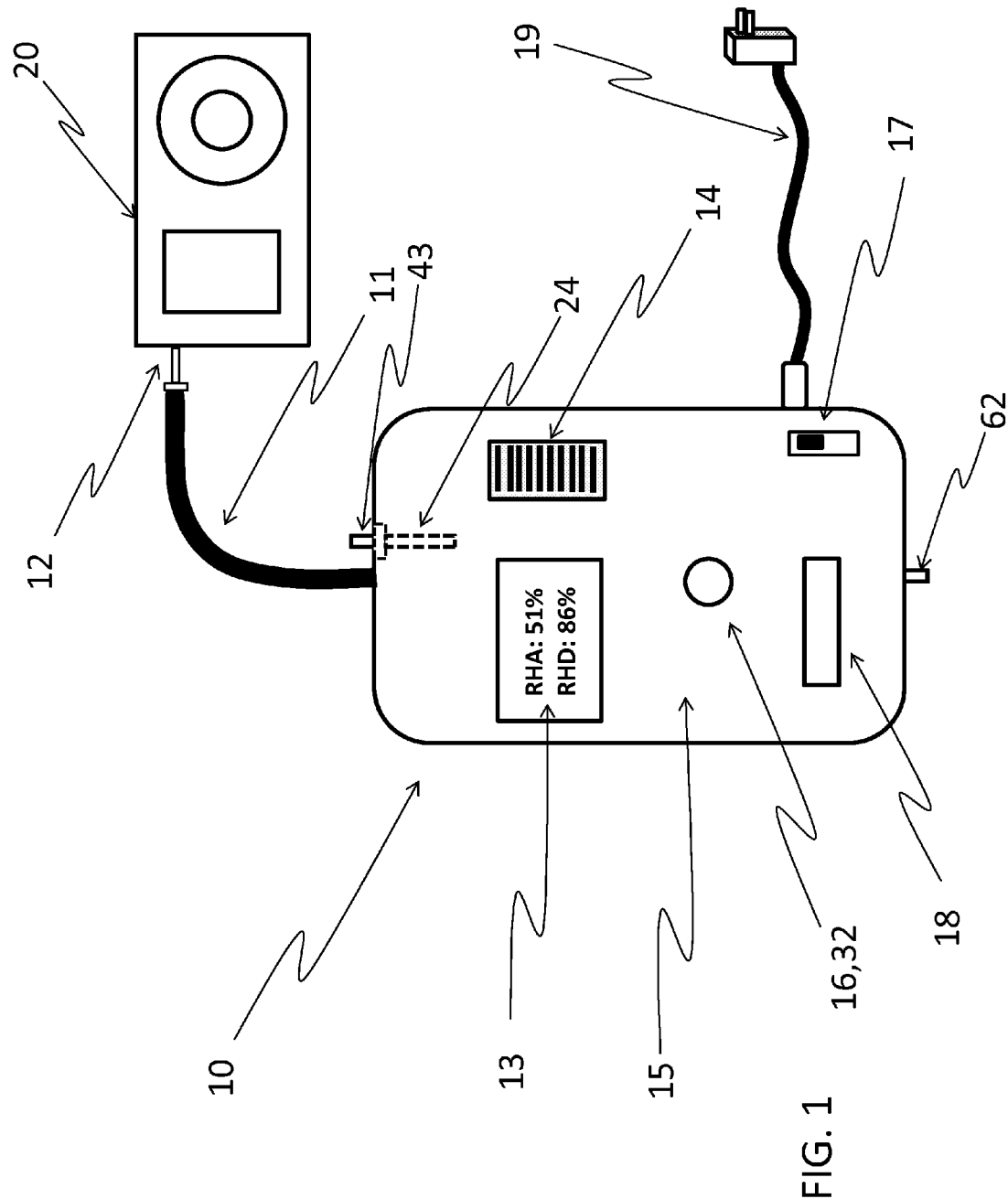
FIG. 1 is an isometric view of a moisture detector and an example device to be tested according to one embodiment of the present disclosure.

For the purposes of promoting an understanding of the principles of the disclosure, reference will now be made to one or more embodiments, which may or may not be illustrated in the drawings, and specific language will be used to describe the same. It will nevertheless be understood that no limitation of the scope of the disclosure is thereby intended; any alterations and further modifications of the described or illustrated embodiments, and any further applications of the principles of the disclosure as illustrated herein are contemplated as would normally occur to one skilled in the art to which the disclosure relates. At least one embodiment of the disclosure is shown in great detail, although it will be apparent to those skilled in the relevant art that some features or some combinations of features may not be shown for the sake of clarity.

Any reference to "invention" within this document is a reference to an embodiment of a family of inventions, with no single embodiment including features that are necessarily included in all embodiments, unless otherwise stated. Furthermore, although there may be references to benefits or advantages provided by some embodiments, other embodiments may not include those same benefits or advantages, or may include different benefits or advantages. Any benefits or advantages described herein are not to be construed as limiting to any of the claims.

Specific quantities (spatial dimensions, temperatures, pressures, times, force, resistance, current, voltage, concentrations, wavelengths, frequencies, heat transfer coefficients, dimensionless parameters, etc.) may be used explicitly or implicitly herein, such specific quantities are presented as examples only and are approximate values unless otherwise indicated. Discussions pertaining to specific compositions of matter, if present, are presented as examples only and do not limit the applicability of other compositions of matter, especially other compositions of matter with similar properties, unless otherwise indicated.

At least one embodiment of the present disclosure includes a moisture sensor (which may also be referred to as a moisture detector) that connects to a port of an electronic device, samples the environment (for example, air) within the electronic device, and detects (and/or senses) the moisture contained in the sampled environment. In some embodiments, the moisture sensor connects to a port (for example, and electrical port) of the electronic device and creates a low pressure region at the port to sample the gas within the electronic device.

Depicted in FIG. 1 is a moisture detecting apparatus 10, which can determine the presence of water or other compound (or molecule) of interest which may be in liquid or gas form in a device under test ("DUT"), according to one embodiment of the present disclosure. In one embodiment, moisture detecting apparatus 10 includes a casing 15, a connector 12 for connecting to a device under test ("DUT") 20, a moisture sensor (for example, DUT moisture sensor 26 depicted in FIG. 4) pneumatically connected to connector 12, a pneumatic pump 27 for delivering gas from the DUT to the moisture sensor, and a display (for example, display 13) for displaying information about the moisture in DUT 20 to a user. An additional display 14, which may take the form of a bar graph (for example, an LED bar graph), may optionally be used.

In use, connector 12 is connected to a DUT (such as by connecting connector 12 to an existing or built-in port of the DUT, for example, a power port, a headphone jack, etc.). When pneumatic pump 27 is actuated, gas from within the DUT is sampled by the moisture sensor, and information about the moisture content of the gas is sensed by the moisture sensor and may be displayed to the user on a display (such as display 13).

The pneumatic pump 27 may be actuated manually by the user (such as by depressing a button such as test initiation button 32). In alternate embodiments, moisture detector 10 is capable of sensing when a DUT is connected, and pneumatic pump 27 and the testing of the DUT can be initiated automatically after the moisture detector determines that it is connected to a DUT.

The display (for example, display 13) may be a simple binary indicator (such as one or more lights, which may be, for example, green and/or red) indicating whether the moisture in the DUT exceeds a particular threshold or not. The threshold may be predetermined at a level intended to indicate that the DUT has been exposed to excessive moisture. In other embodiments, the display may display more information, such as the level of moisture (for example, humidity) within the DUT. In other embodiments, display 13 may display the moisture information as characters. For example, such information may be displayed as, for example, "RHA" (Relative Humidity Atmosphere).

Moisture detector 10 may also include an optional power switch 17, an optional calibration switch 16, and an optional test switch 32. One or more of switches 16, 17 and 32, if used, may be the same physical switch in various embodiments of the present disclosure.

Embodiments of moisture detector 10 may also include an optional power connector 19 (for example, an AC power adapter), for supplying power to moisture detector 10. Some embodiments of moisture detector 10 have an internal power source (for example, a battery) and may not include power connector 19 or may include a power connector in addition to the internal power source.

Moisture detector 10 may also include an optional printer 18, which may be used to record test information in a more permanent form, such as on a piece of paper.

Moisture detector 10 optionally includes a sampling tube 11 connecting connector 12 to the moisture sensor. Sampling tube 11 may be flexible, and may be an elastomeric tube with an inner diameter adapted to attach to connector 12.

Figure 2:
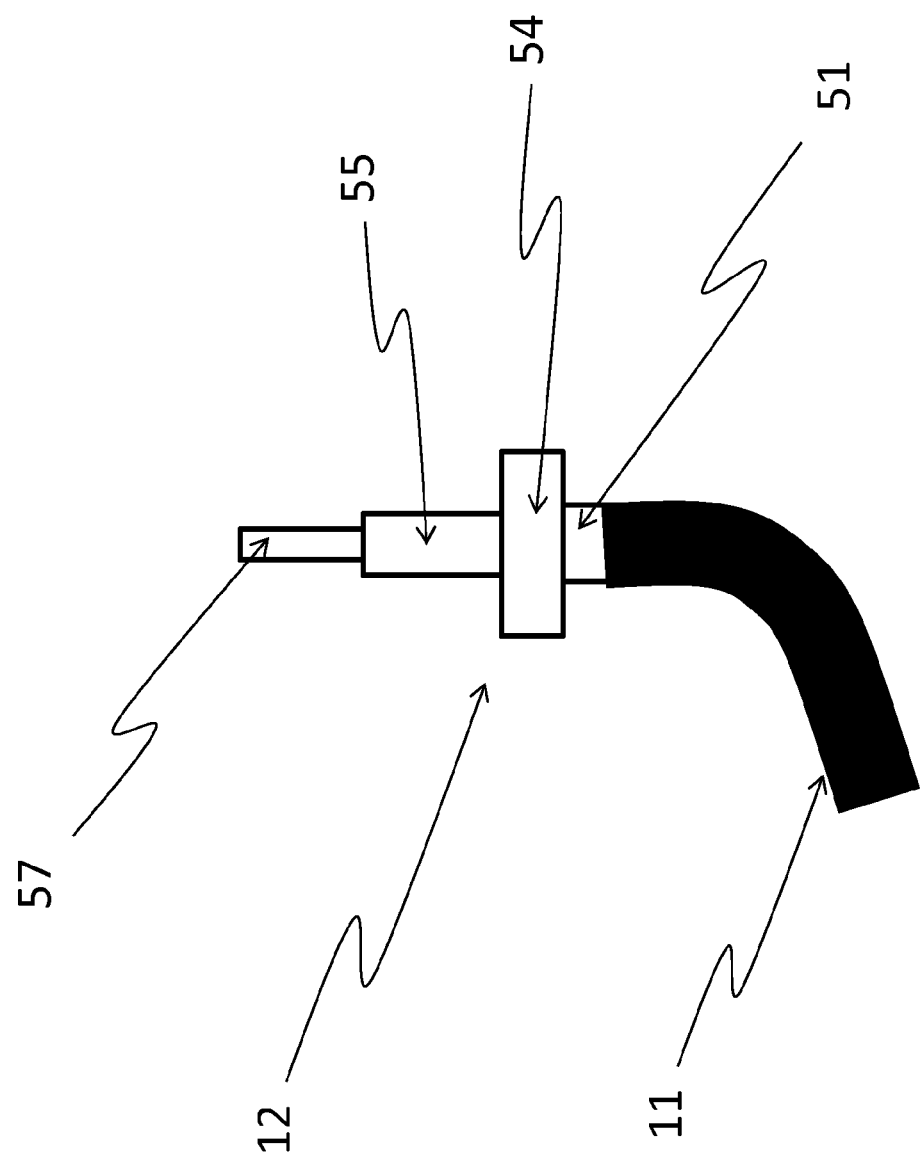
FIG. 2 is a partial plan view of a connector associated with the moisture detector depicted in FIG. 1 according to one embodiment of the present disclosure.
Figure 3:
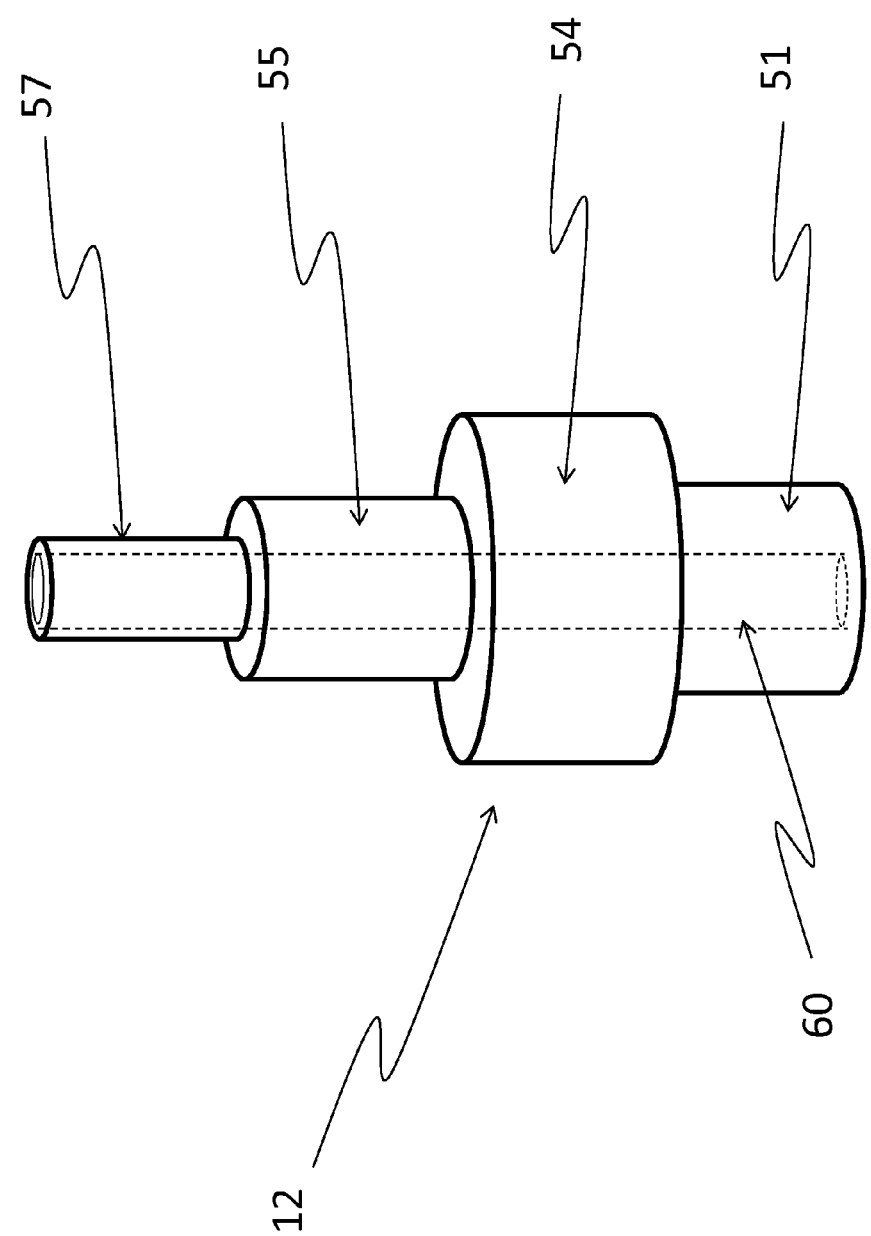
FIG. 3 is a partial perspective view of the connector depicted in FIG. 2.

Example embodiments of DUT connector 12 and a portion of DUT air sampling tube 11 are depicted in FIG. 2. Connector 12 includes a body portion 54 (which may be enlarged with respect to the rest of connector 12, such as to facilitate gripping by the user), a connector 51 (which may be adapted to connect to sampling tube 11), and an air sampling orifice 60 extending through connector 12.

Connector 12 may be adapted to fit more than one type of DUT port, such as a headphone jack (which are provided with almost any type of portable electronic device), power connector, or data connector. For example, connector 12 may have more than one sampling port sections, each adapted to fit a different size or type of port on a DUT. For example, connector 12 may have a sampling port section 57 and a larger air sampling port section 55 with a diameter larger than the diameter of sampling port section 57. In one embodiment, the diameter of the larger section 55 is sized to fit a standard 3.5 mm headphone jack for an electronic device, and the smaller sampling port section 57 is sized to fit a standard 2.5 mm headphone jack. Still further embodiments of connector 12 are adapted to connect to standard power connecters (mini USB and the like) utilized on various portable electronic devices, which may be used as air-sampling ports as well.

In at least the depicted embodiment, connector 12 includes an air sampling tube connector stub 51 that is connected via an air-tight friction-fit engagement to DUT air sampling tube 11.

Connector 12 may be molded or machined out of a solid, homogeneous piece of material, for example a polymeric or metal material. In other embodiments, connector 12 can be fabricated from several pieces that are connected to one another, such as by threading, tapping, or by an interference fit (for example a press fit). Connector 12 may also be fabricated of a suitable material to inhibit corrosion or the formation of iron oxide, which may have certain advantages in inhibiting rust build up from repeated contact with moisture laden portable electronic devices. Example materials include polymers, stainless steel, aluminum, and/or steel with a suitable coating to name but a few.

An exhaust port 62 may be used to exhaust the gas sampled from DUT 20 back to the atmosphere from moisture detector 10.

An airflow sensor (for example, a vacuum sensor 25) may also be included in some embodiments of moisture detector 10. Vacuum sensor 25 may be used, for example, to improve the accuracy of the moisture measurements, calibrate moisture detector 10, and/or detect possible malfunctions of the moisture detector 10, such as a partial or total failure of pneumatic pump 27

Moisture detector 10 optionally includes a means for detecting moisture in the ambient air. In these embodiments, an ambient air sampling port, for example ambient air sampling orifice 43, is used to introduce ambient air into moisture detector 10. Ambient air sampling orifice 43 is pneumatically connected to a moisture sensor, such as DUT moisture sensor 26 or an optional ambient air moisture sensor 23. A pneumatic pathway 24 may be used to connect orifice 43 and the moisture sensor and direct ambient air to the moisture sensor. In some embodiments, the internal passageway of orifice 43 is pneumatically similar to the internal passageway of connector 12, while in still further embodiments the shape of orifice 43 is substantially similar to the shape of connector 12. An exhaust port 62 may be used to exhaust the ambient air back to the atmosphere from moisture detector 10.

In some embodiments, ambient air sampling orifice 43 is positioned where it will be located away from the user's hand during use, which may have advantages in reducing the ability of moisture from the user's hand to enter moisture detector 10 through orifice 43 (such as through evaporation from the user's hand) and have adverse effects on the moisture measurements. Exhaust port 62 may also be located away from orifice 43 to prevent contamination of the ambient air sample with air being discharged from pump 27.

Figure 9:
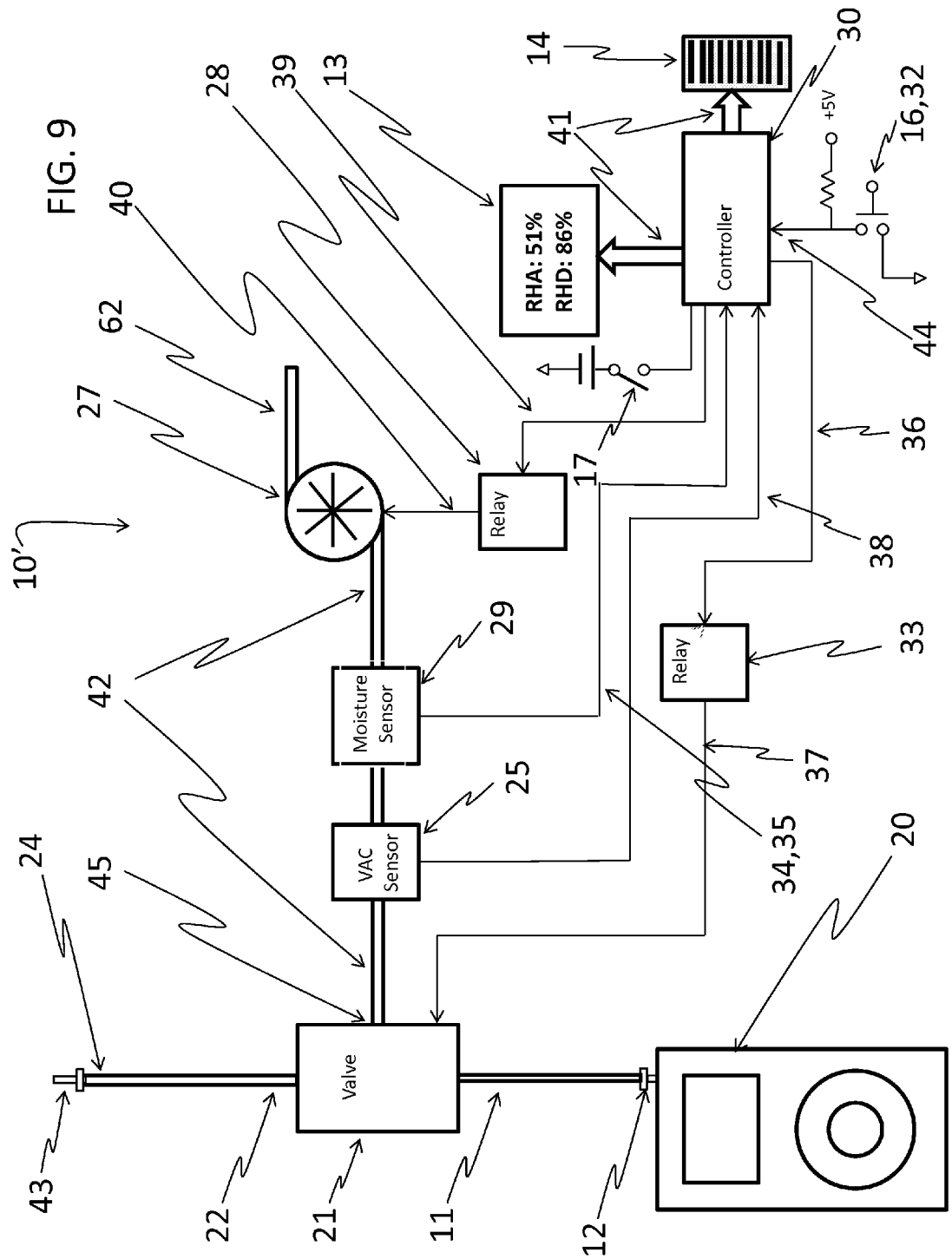
FIG. 9 is a schematic view of moisture detector with a common moisture sensor according to one embodiment of the present disclosure.
Figure 10:
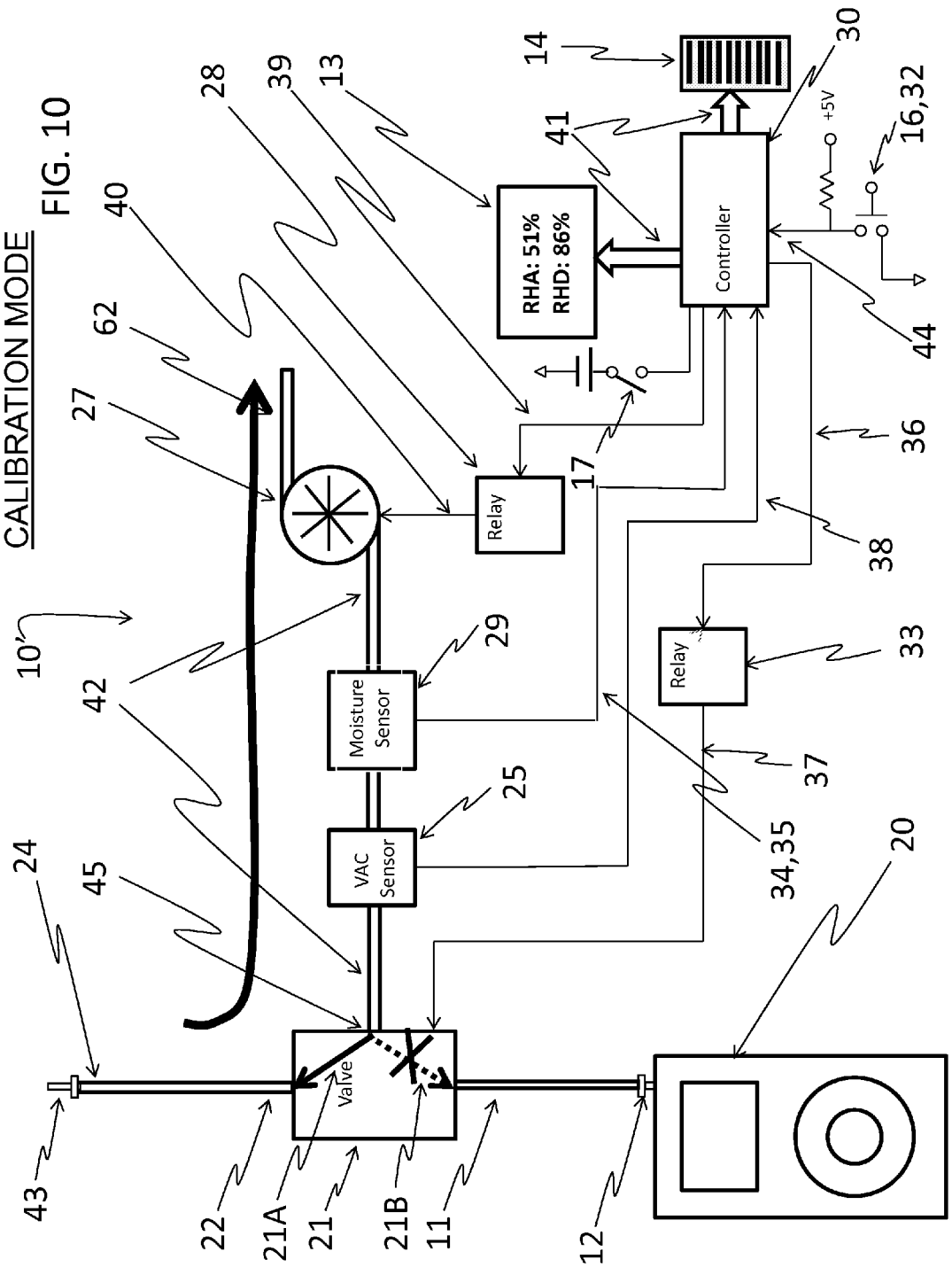
FIG. 10 is a schematic view of an example mode of operating the moisture detector depicted in FIG. 9 according to one embodiment of the present disclosure.
Figure 11:
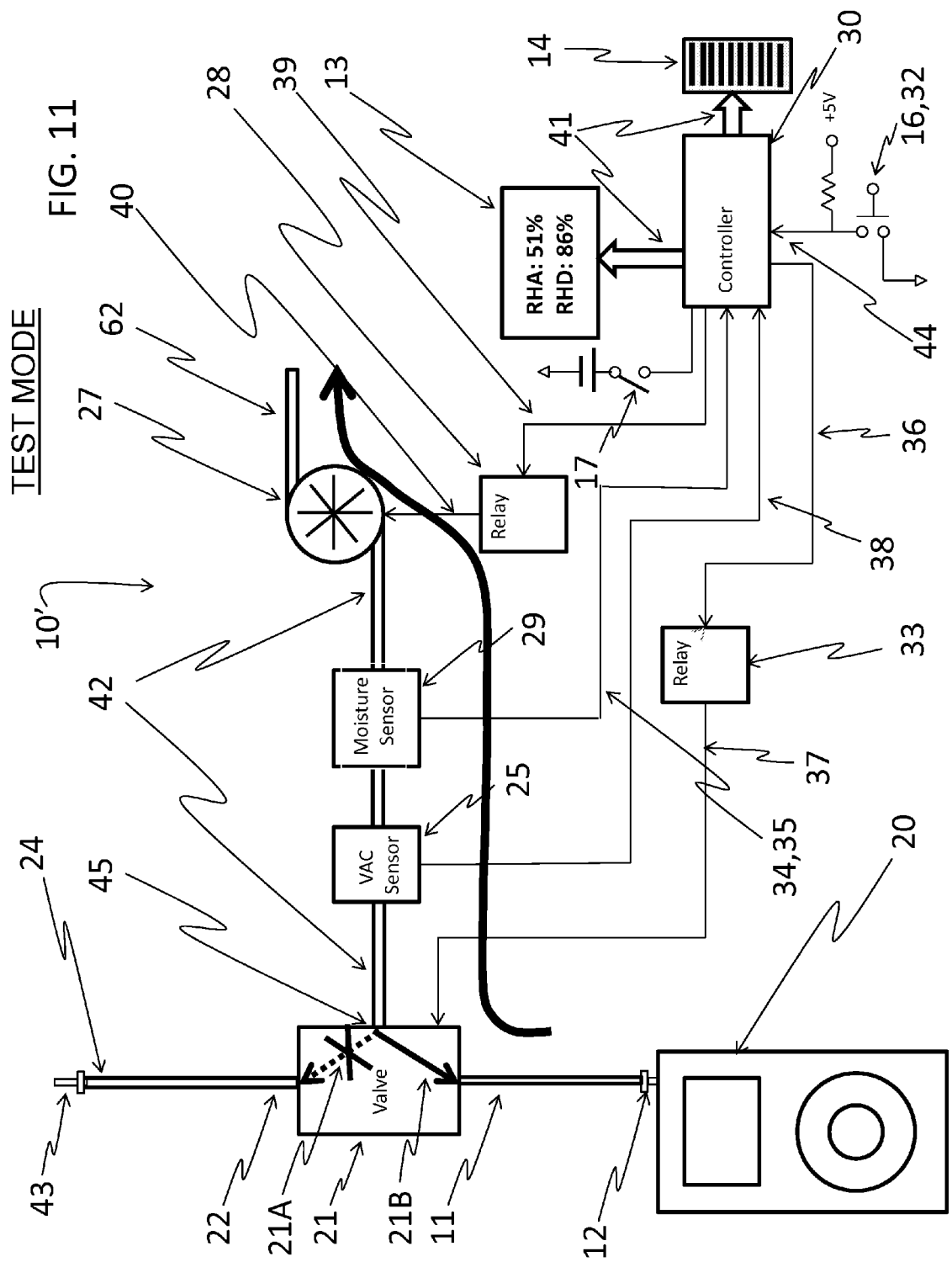
FIG. 11 is a schematic view of another example mode of operating the moisture detector depicted in FIG. 9 according to another embodiment of the present disclosure.

Depicted in FIGS. 9-11 is a moisture sensor 10' with a common moisture sensor 29, which samples both atmospheric gas and DUT gas depending on the position of pneumatic valve 21. Common moisture sensor 29 senses and provides moisture signals for gas sampled from both ambient conditions and from the DUT. The components in FIGS. 9-11 with similar numbers to the components in FIGS. 1-6 operate in a similar fashion to those described with respect to FIGS. 1-6. With moisture sensor 29 being downstream of valve 21, the switch position of valve 21 determines whether sensor 29 senses ambient or DUT gas.

In embodiments where ambient air is also sampled, moisture detector 10 may also include an optional 3-way valve, for example 3-way valve 21.

In embodiments utilizing a single moisture sensor (for example, moisture sensor 29) for sensing moisture in both the gas from the DUT and the ambient air, the 3-way valve 21 is typically located upstream of the moisture sensor and controls which gas (ambient or DUT) is drawn into the moisture sensor by the pneumatic pump 27, which is located downstream from the moisture sensor.

In embodiments utilizing two moisture sensors (for example, moisture sensors 26 and 23), the 3-way valve is typically located downstream of the two moisture sensors and upstream of pneumatic pump 27 to control the connection of the sensors (ambient and/or DUT) to vacuum source. In these embodiments, DUT 20 may be pneumatically connected to a 3-way pneumatic valve 21 via a DUT sampling tube 11, DUT moisture sensor 26, and connector 12.

In embodiments utilizing ambient air moisture sensor 23, sensor 23 can be connected to 3-way pneumatic valve 21 via a pneumatic pathway 22.

When used, valve 21 may be actuated via a driver signal 37 coming from a pneumatic valve relay 33 (which may be solid state), which may be switched (for example, digitally switched) via a 3-way valve digital control signal 36 from controller 30.

In embodiments where ambient air is also sampled, a common pneumatic pathway 42 may be used by pneumatic pump 27 to draw air through connector 12 and orifice 43. In one example (see, for example, FIG. 4), common pneumatic pathway 42 is pneumatically connected to 3-way valve 21 at a common pneumatic port 45. Pathway 42 connects 3-way pneumatic valve 21 to pneumatic pump 27, and to vacuum sensor 25 (if used).

Figure 4:
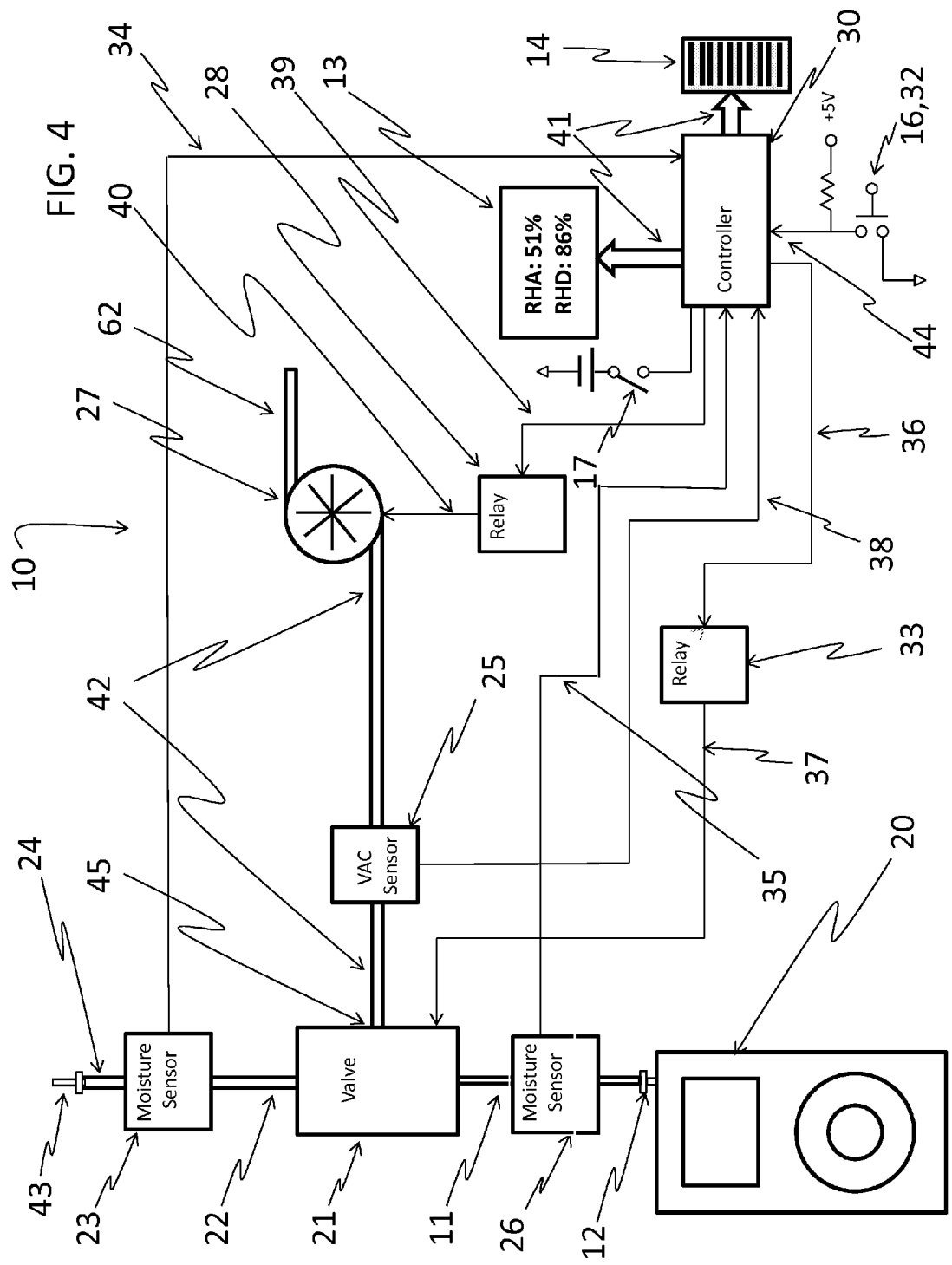
FIG. 4 is a schematic view of an embodiment of the moisture detector depicted in FIG. 1.

Referring now to FIG. 4, moisture detector 10 may include a controller 30 (for example, a control microprocessor). Controller 30 includes control code to control operation of moisture detector 10 and is connected to one or more components of moisture detector 10.

Controller 30 may be electrically connected to display 13 and/or additional display 14 (if used), such as via a data bus 41. Various messages and/or status indicia may be displayed on display 13 and/or 14.

DUT moisture sensor 26 may be connected to controller 30, and a feedback signal 35 may be used by controller 30 to obtain information (for example, relative humidity information) from sensor 26 a test or to calibrate the system.

Controller 30 may also be electrically connected to an optional test button 32, such as through digital input 44. Calibration button 16, which may be the same physical device (for example, button) as test switch 32, is shown schematically in FIGS. 4-6.

Vacuum sensor 25 (if used) can be connected to controller 30, and a feedback signal 38 can be used by controller 30 to poll vacuum sensor 25 for calibration purposes.

Pneumatic pump 27 may be connected to controller 30, and this connection may include an optional relay 28 (which may be a solid state relay). Control signal 39 can control the on-off operation of pneumatic pump 27, such as via a pneumatic pump actuation signal 40 from relay 28.

Ambient air moisture sensor 23 (if used) may be connected to a controller 30, such as via a room ambient relative humidity feedback signal 34, and may be used to supply information about the ambient conditions to controller 30, which may be used to increase the accuracy of moisture detector 10, calibrate moisture detector 10, and/or to determine ambient moisture/humidity conditions.

Figure 5:
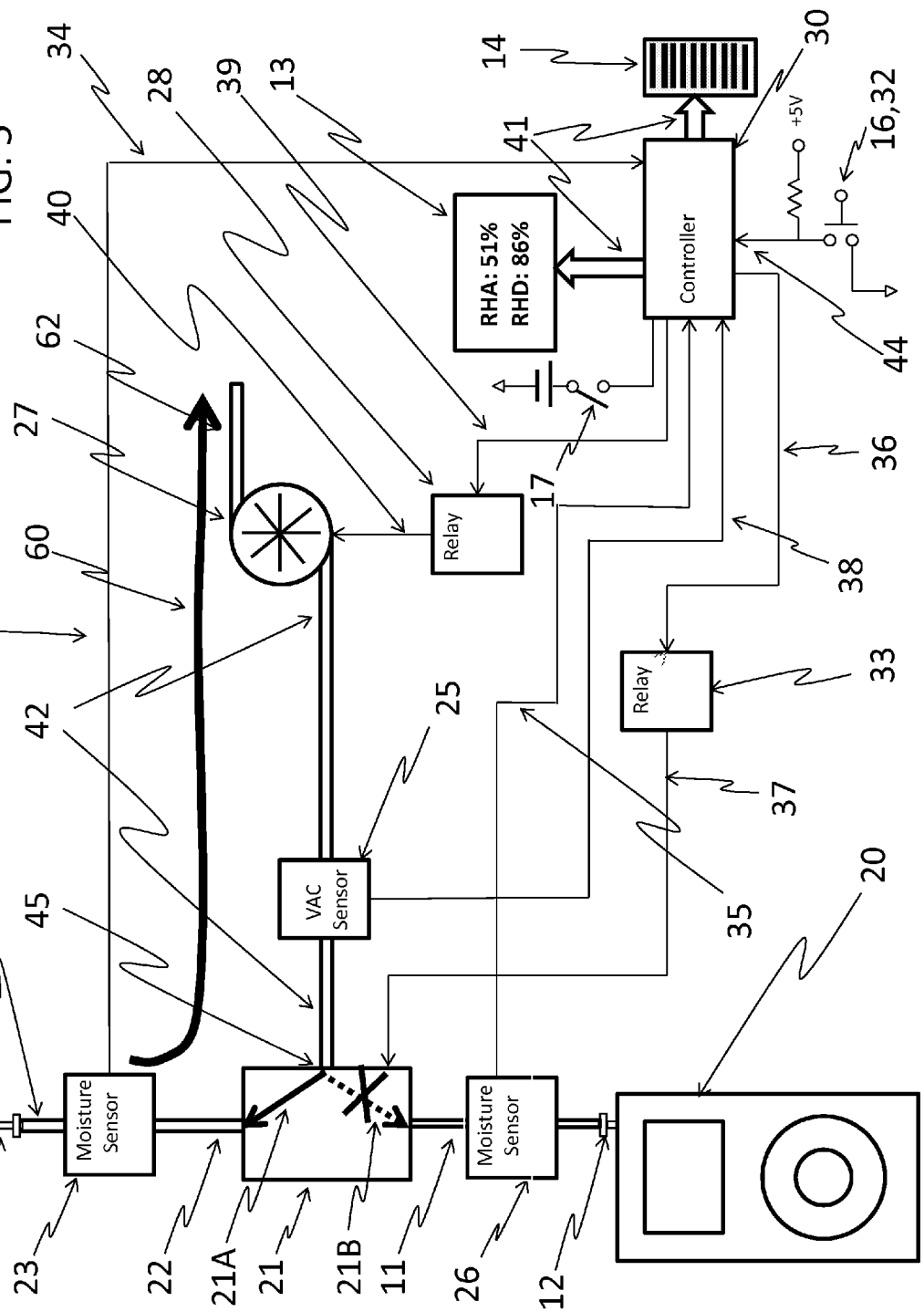
FIG. 5 is a schematic view of an example mode of operating the moisture detector depicted in FIG. 1 according to one embodiment of the present disclosure.

FIG. 5 depicts an example calibration mode of moisture detector 10 utilizing an embodiment with a moisture sensor (for example, DUT moisture sensor 26 and/or ambient air moisture sensor 23), an optional 3-way valve 21, and a vacuum sensor 25 according to at least one embodiment of the present disclosure. In the example calibration mode, 3-way pneumatic valve 21 is pneumatically switched to facilitate air flowing through room ambient pneumatic sampling circuit 21A and restrict (and/or inhibit) gas from entering DUT pneumatic sampling circuit 21B. Ambient sampled airflow 60 is pulled by pneumatic pump 27 through ambient sampling orifice 43, ambient moisture sensor 23, pneumatic pathway 22, valve 21, common pneumatic pathway 42, and vacuum sensor 25. Ambient air is exhausted via exhaust port 62. In some embodiments, exhaust port 62 is mounted away from orifice 43 (and/or connector 12), such as being disposed on the opposite side of casing 15 from orifice 43 (and/or connector 12).

Software routines in controller 30 toggle 3-way driver signal 37 to an orientation (which may be referred to as logic 1), which energizes 3-way pneumatic valve solid state relay 33, switching 3-way pneumatic valve 21 into the calibration state, which in turn pneumatically blocks DUT pneumatic sampling circuit 21B and opens room ambient pneumatic sampling circuit 21A as shown in FIG. 5. (In embodiments with a single moisture sensor, the ambient sampling orifice 43 will be connected to the moisture sensor while the connector 12 is disconnected from the moisture sensor).

Controller 30 polls ambient air moisture sensor 23 via room ambient relative humidity feedback signal 34 and, in embodiments utilizing a vacuum sensor 25, may poll vacuum sensor 25 via vacuum sensor feedback signal 38. In embodiments where both sensor 23 and sensor 25 are polled, such polling may be accomplished simultaneously or sequentially. Using software conversion routines, controller 30 can establish ambient moisture conditions (for example, relative humidity) with respect to the measured atmospheric pressure from vacuum sensor 25. These values may be stored and used to establish a baseline room moisture content (for example, relative humidity) as compared to vacuum pressure. Once these baseline values are determined, controller 30 can invoke software routines to display the ambient moisture conditions on display 13 via signals sent electrically through data bus 41.

Pneumatic pump 27 is energized, such as via pneumatic pump actuation signal 40 from pneumatic pump control relay 28 and pneumatic pump digital control signal 39 from controller 30. Pneumatic pump 27 pulls air through common pneumatic pathway 42, vacuum sensor 25, ambient air moisture sensor 23, room ambient pneumatic pathways 22 and 24 and room ambient sampling orifice 43. A reduced vacuum pressure occurs in the pneumatic circuit with airflow 60 due to the restriction of room ambient sampling orifice 43 (which may have a similar opening as connector 12), thereby creating a low pressure region within orifice 43 for drawing ambient air into moisture detector 10.

Reduced vacuum pressure, which may be sensed by controller 30 (when used) via vacuum sensor 25 and vacuum sensor feedback signal 38, may be sampled and stored as a vacuum pressure value. Controller 30 may also sample ambient air moisture sensor 23 via room ambient relative humidity feedback signal 34, and may also store that value for later use. These values may be stored in memory within the controller 30, and may be used to provide a correction factor to the raw (uncorrected) ambient and/or DUT moisture indication. The ambient air moisture sensor 23 and/or the DUT moisture sensor 26 can provide false (for example, lower) indications of moisture due to, for example, the speed in which the sampled air flows through, past and/or near sensor 23 and/or sensor 26 due to pneumatic pump 27. This increased speed of air flow may reduce the accuracy of sensors 26 and/or 26 due to mass transport evaporation. The vacuum pressure readings and resulting relative humidity readings may be stored in controller 30 (such as in the form of look-up variables), and provide a scaling mechanism for relative humidity adjustments due to the presence of reduced vacuum pressures and/or the speed of the airflow through the sensor(s) during the software test routine.

As air is pulled across DUT moisture sensor 26 via pneumatic pump 27 (active airflow), the resulting sensor response tends to be different (for example, lower) than the resulting sensor response with no air flow (static situation) across sensor 26. This same effect can occur with any moisture sensor, such as ambient moisture sensor 23. It is thought that this false reading with active airflow is a result of air flowing over the moisture sensors and causing additional evaporation to occur by virtue of the air being passed across the sensors.

Various embodiments of moisture detector 10 compensate for these inaccuracies. For example, some embodiments use ambient moisture (as detected by ambient moisture sensor 23 and/or DUT moisture sensor 26 depending on the particular architecture of the embodiment) to correct the raw moisture measurements of the DUT sensor 26 and improve the accuracy of moisture detector 10. One exemplary implementation includes controller 30 sampling ambient moisture (such as by receiving data from sensor 23 and/or 26) during a static situation with no airflow induced by pneumatic pump 27. Controller 30 also samples ambient moisture while drawing gas (e.g., air) through the moisture sensor using pneumatic pump 27 to produce airflow across the moisture sensor. Using the static and active moisture measurements, a correction factor for the moisture sensor can be computed in controller 30, and the correction factor can be applied to the raw moisture measurements of moisture sensor when sampling the DUT.

In embodiments with vacuum sensor 25, data can be collected for various values of airflow and correction factors can be calculated for various airflows.

In some embodiments, the opening of orifice 43 is pneumatically similar to the opening of connector 12. In these embodiments, the airflow restriction of orifice 43 is similar to the airflow restriction of connector 12 resulting in similar conditions within the sensor during test and calibration, which can simplify the computations required to generate the correction factors.

In embodiments without the optional 3-way valve, the calibration mode may be run using connector 12 to draw ambient air into moisture detector 10 before (or after) connector 12 is connected to the DUT.

FIG. 10 depicts an example calibration mode of a moisture detector 10' utilizing an embodiment with a moisture sensor (for example, common moisture sensor 29), a 3-way valve 21, and an optional vacuum sensor 25 according to at least one embodiment of the present disclosure. The components in FIG. 10 with similar numbers to the components in FIG. 5 operate in a similar fashion to those described with respect to FIG. 5. With moisture sensor 29 being downstream of valve 21, the switch position of valve 21 determines whether sensor 29 senses ambient or DUT gas.

Figure 6:
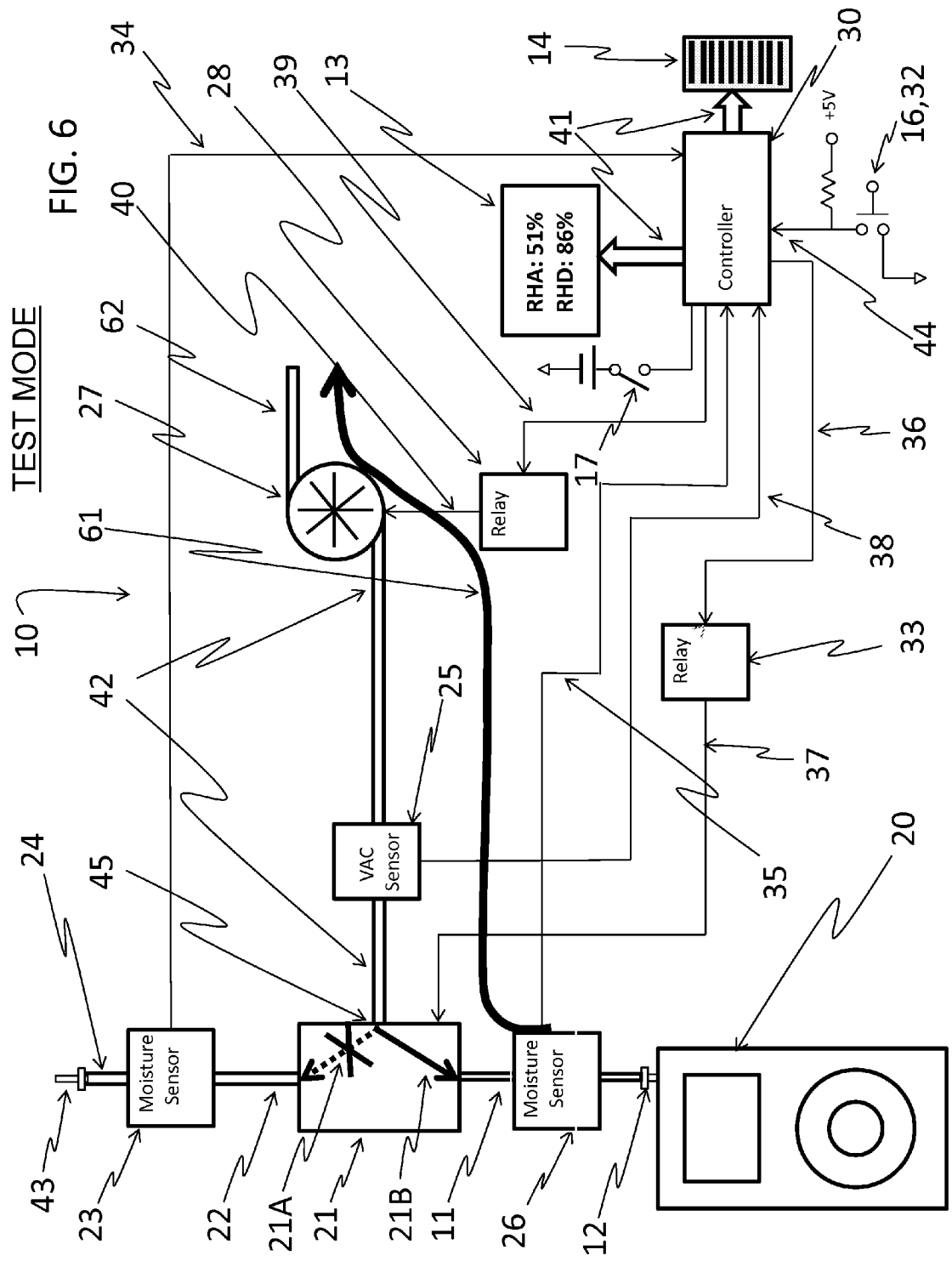
FIG. 6 is a schematic view of another example mode of operating the moisture detector depicted in FIG. 1 according to another embodiment of the present disclosure.

FIG. 6 depicts an example test mode of moisture detector 10 utilizing an embodiment with a moisture sensor (for example, DUT moisture sensor 26), an optional 3-way valve 21, and a pneumatic pump 27 according to at least one embodiment of the present disclosure. In the example test mode, 3-way pneumatic valve 21 is pneumatically switched to facilitate air flowing through DUT pneumatic sampling circuit 21B and restrict (and/or inhibit) ambient from entering room ambient pneumatic sampling circuit 21A. DUT sampled airflow 61 is pulled by pneumatic pump 27 from the device under test (DUT) and through connector 12, DUT moisture sensor 26, pneumatic pathway 11, valve 21, common pneumatic pathway 42, and vacuum sensor 25. DUT gas air is exhausted via exhaust port 62.

Software routines in controller 30 toggle 3-way driver signal 37 to an orientation (which may be referred to as logic 0), which de-energizes 3-way pneumatic valve relay 33, switching 3-way pneumatic valve 21 into the test state, which in turn pneumatically opens DUT pneumatic sampling circuit 21B and blocks room ambient pneumatic sampling circuit 21A. In alternate embodiments, the state of valve 21 (in other words, the energized or de-energized nature of valve 21) relative to being in either the calibration or test mode may be different.

In embodiments with a single moisture sensor, connector 12 will be connected to the moisture sensor while the ambient sampling orifice 43 is disconnected from the moisture sensor.

Controller 30 polls DUT moisture sensor 26 via DUT relative humidity feedback signal 35 and, in embodiments utilizing a vacuum sensor 25, may poll vacuum sensor 25 via vacuum sensor feedback signal 38. Using software conversion routines, controller 30 can establish DUT moisture conditions (for example, relative humidity) with respect to the measured atmospheric pressure from vacuum sensor 25. The raw DUT moisture level detected may then be displayed.

In some embodiments, the raw DUT moisture level is corrected using a correction factor (such as one derived during the calibration mode) to compute a corrected moisture level. In one embodiment, the raw moisture level can be corrected using a correction factor that is scaled (such as by using curve fitting routine such as, for example, linear interpolation) for the actual vacuum level sensed by vacuum sensor 25 during testing. The corrected moisture level may then be displayed to the user, such as by controller 30 invoking software routines to display the corrected DUT relative humidity on character display 13 via signals sent electrically through data bus 41.

FIG. 11 depicts an example test mode of a moisture detector 10' utilizing an embodiment with a moisture sensor (for example, common moisture sensor 29), a 3-way valve 21, and an optional vacuum sensor 25 according to at least one embodiment of the present disclosure. The components in FIG. 11 with similar numbers to the components in FIG. 6 operate in a similar fashion to those described with respect to FIG. 6. With moisture sensor 29 being downstream of valve 21, the switch position of valve 21 determines whether sensor 29 senses ambient or DUT gas.

In some embodiments, controller 30 converts sensor signals from sensor 23, sensor 25 and/or sensor 26 (which may be obtained by controller 30 control code invoking sampling routines to poll one or more of these sensors via signals 34, 38, and 35) to information usable by one or more displays (for example, digital character information) and displays the ambient relative humidity and/or DUT relative humidity (corrected and/or uncorrected) on a display. In at least one embodiment, the information on display 13 is displayed as characters, which may be accomplished by sending data and handshaking signals across electrical data bus 41. Such information may be displayed as, for example, "RHA" (Relative Humidity Atmosphere) and "RHD" (Relative Humidity Device) as shown in FIGS. 1 and 4-6. Controller 30 may also convert DUT relative humidity feedback signal to a scaled 10-bit digital data signal and display this information on a second display, such as by writing this information to LED bar graph 14 via common data bus 41.

In some embodiments, the calibration mode runs prior to the test mode. In alternate embodiments, the test mode can run prior to the calibration mode.

Figure 7:
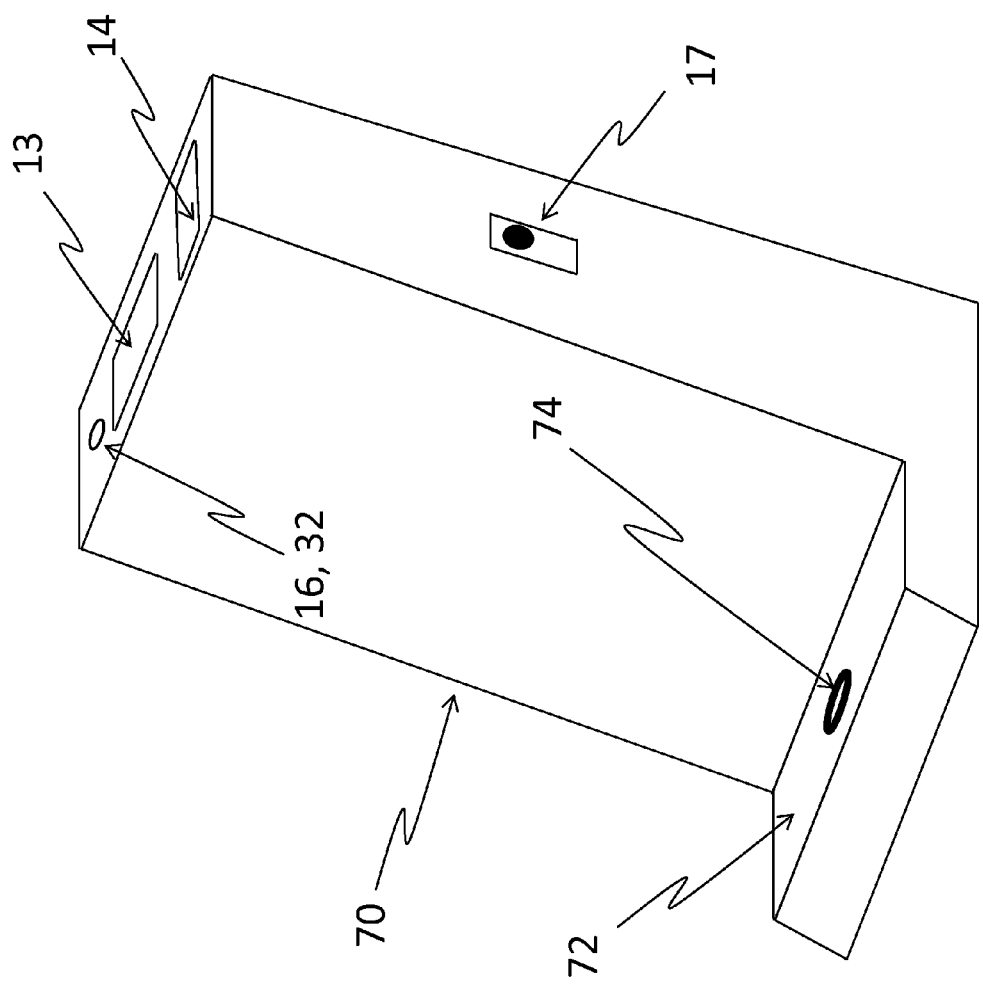
FIG. 7 is a perspective view of a moisture detector according to another embodiment of the present disclosure.

FIG. 7 depicts a moisture detector according to another embodiment of the present disclosure. Enclosure cradle 70 is shown with an optional display 13, a device under test ("DUT") sampling port 74, an optional DUT sampling port sealing surface 72, and an optional LED bar graph 14. Sealing surface 72 provides pneumatic sealing for DUT 20 and enclosure cradle 70 and permits DUT sampling port 74 to sample air from DUT 20 headphone jack or power port.

Figure 8:
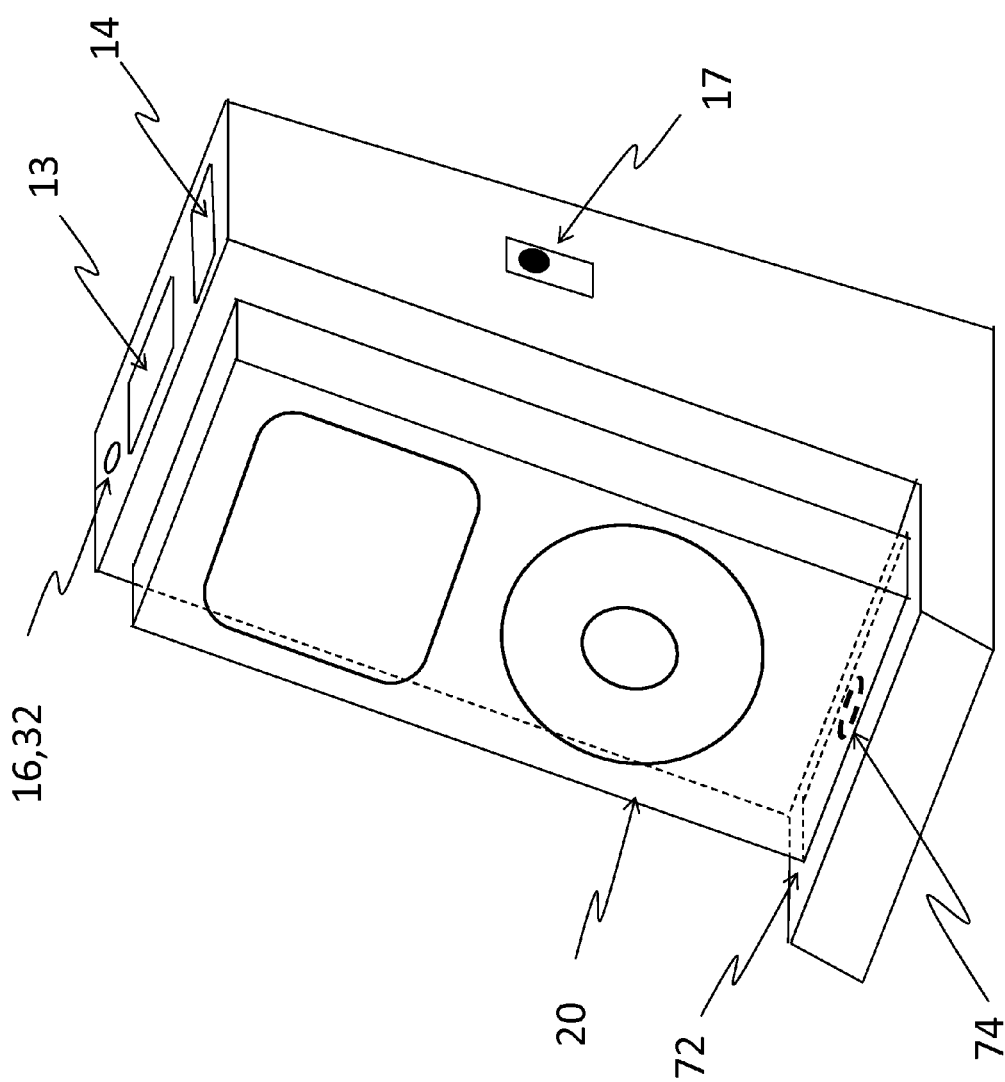
FIG. 8 is a perspective view of the moisture detector depicted in FIG. 7 connected to an example device to be tested.

FIG. 8 depicts the moisture sensing apparatus from FIG. 7 with DUT 20 connected to DUT air sampling port 74 and in contact with DUT sampling port sealing surface 72. The functioning of the moisture sensing apparatus depicted in FIGS. 7 and 8 is as described above with respect to the embodiments and alternative embodiments depicted in FIGS. 1-6.

In use, a device (for example, a portable electronic device) which may be suspected of having moisture levels that could inhibit operation of the device (such as by being dropped in water or other liquid, or by being exposed to high-humidity environments), is connected to connector 12/74, which may be adapted to connect with one or more ports of the device under test (DUT) (for example, a headphone or power jack).

In embodiments requiring user input to power up the moisture detector, the power switch (for example, power switch 17) is then turned to the "on" position, which provides electrical power to the device and its componentry. Alternate embodiments can detect when a DUT is connected to the moisture detector and automatically power up. Controller 30 may be provided with non-volatile memory in order to permanently store software control code.

After the moisture detector powers up, the user may then initiate the calibration mode, such as by pressing calibration button 16 (which may be the same button as test switch 32), which is shown schematically in FIGS. 4-6. Alternate embodiments automatically initiate the calibration mode, such as after a certain amount of time has lapsed after power up and/or when the moisture detector senses that the connector 12/74 is connected to a DUT (such as in embodiments utilizing a DUT moisture sensor 26 and a separate ambient moisture sensor 23) or is not connected to a DUT (such as in embodiments utilizing a single moisture sensor).

Controller 30 may determine whether to power up/down the moisture detector, to initiate a calibration cycle, or to initiate a test cycle based on the type of input received from one or more input buttons. For example, in one embodiment controller 30 samples electrical switch signal 44 (see FIG. 4) and invokes a timer circuit to measure the length of time the electrical switch 16/32 is depressed. If the user holds the test and calibration button down for more than set duration (for example, at least 1 second but less than 5 seconds), controller 30 determines that the user desires to run an actual "test" routine in order to test for the presence of moisture in DUT 20. If the user holds a test/calibration button down for more than, for example, 5 seconds, controller 30 determines that the user desires to run the "calibration" routine (or possibly to power down the moisture sensor). The times indicated herein are presented for purposes illustration only; anyone skilled in the art of microcontroller software control will understand such times can be easily modified to meet user preference. Any combinations or subcombinations of these times can provide the desired effect of using one common push button to achieve a calibration signal, a test signal, and/or a power signal being sent to controller 30.

The moisture detector may also initiate a test cycle automatically after detecting connection to a DUT 20.

Once the test mode has been initiated (which may occur before calibration in some embodiments), pneumatic pump 27 is energized, for example, via pneumatic pump actuation signal 40 derived from pneumatic pump control relay 28 and pneumatic pump control signal 39 that is driven from controller 30 under software control. Pneumatic pump 27 then pulls air through DUT moisture sensor 26 and, in embodiments with a vacuum sensor 25, through vacuum sensor 25. A reduced pressure occurs in the pneumatic circuit with airflow 61. The reduced pressure (which may be sensed by controller 30 via vacuum sensor 25 and vacuum sensor feedback signal 38) may be sampled and stored as a vacuum pressure value. DUT moisture sensor 26 may be sampled and the sample value also stored via DUT relative humidity feedback signal 35. These values may then be mathematically scaled using the correction factors derived from the calibration routine. The scaled DUT moisture level (for example, relative humidity numerical result) may then be electrically written across data bus 41 and displayed on display 13 as the DUT relative humidity ("RHD").

Controller 30 may also compute the difference between the room ambient relative humidity and the corrected DUT moisture level, and that difference may be used to create a look-up table in controller 30. Controller 30 may also provide an electrical signal across data bus 41 and may also display a scaled difference on LED bar graph 14. Thus, the moisture detecting apparatus 10 can determine the moisture level in a device under test 20 (for example, a portable electronic device), which can be used for further diagnostic and/or repair purposes as desired.

Alternate embodiments of the present disclosure include a moisture detector similar to moisture detector 10 depicted in FIGS. 4-5 without a 3-way valve 21. In one variation, actuation of pneumatic pump 27 results in air flowing simultaneous through sensor 23 and sensor 26, similar to if both circuits in valve 21 could be actuated simultaneously. In an alternate variation, sampling circuits 21A and 21B are physically separate with each sensor having a separate pneumatic pump and optional vacuum sensor. In this alternate variation, gas is drawn through sensor 23 with one pneumatic pump, and gas is drawn through sensor 26 with another pneumatic pump.

Casing 15 is may be fabricated of, for example, a known polymer plastic, glass, or metal, with suitable thickness and geometry to withstand handling by technicians or consumers. In certain embodiments, casing 15 is made from light weight ABS polymer plastic for strength and toughness. In other embodiments, casing 15 can be made of elastomeric material to withstand handling from human oils and acids.

Moisture detector 10 may also be adapted to detect moisture in a variety of situations. For example, moisture detector 10 can sample moisture in electronic devices, bulk materials (including agricultural materials such as grain or seeds), in enclosed spaces such as walls, etc.

Various Aspects of Different Embodiments of the Present Disclosure are Expressed in Statements X1, X2, X3, X4, X5, X6, X7, X8, X9, X10, X11, and X12 as Follows:

X1. A moisture detector, comprising: one or more moisture sensors; and a connector operatively connected to the one or more moisture sensors, the connector adapted to connect to an external port of an electronic device; wherein the one or more moisture sensors receive gas moved from the electronic device and through the connector connected to the external port of the electronic device, and wherein the one or more moisture sensors determine the presence of moisture within the gas moved from the electronic device.

X2. A method, comprising: connecting a moisture detector with one or more moisture sensors to an external port of an electronic device; and detecting moisture within the electronic device with the one or more moisture sensors.

X3. A method, comprising: sampling gas from within an electronic device by generating a low pressure region within the electronic device; detecting the moisture level within the gas from the electronic device; detecting the level of low pressure generated; and generating a modified moisture level output by modifying the measured moisture level using the detected level of low pressure.

X4. A method, comprising: sampling gas from within an electronic device by generating a low pressure region within the electronic device; detecting the moisture level within the gas from the electronic device; sampling ambient air from outside the electronic device; detecting the moisture level within the ambient air; and calculating the moisture level within the electronic device using the detected moisture level within the gas from the electronic device, and the detected moisture level within the ambient air.

X5. An apparatus, comprising: means for connecting a moisture sensor to an electronic device; means for moving gas from within the electronic device to the moisture sensor; and means for detecting moisture in the gas.

X6. A device for detecting moisture in an electronic device substantially as described herein with reference to the accompanying Figures.

X7. A method for detecting moisture in an electronic device substantially as described herein with reference to the accompanying Figures.

X8. A method for manufacturing a moisture detector substantially as described herein with reference to the accompanying Figures.

X9. A moisture detector, comprising: one or more moisture sensors; and a connector operatively connected to the one or more moisture sensors, the connector adapted to connect to an external port of an electronic device; wherein the one or more moisture sensors determine the presence of moisture within the electronic device.

X10. A method, comprising: sampling gas from within an electronic device by generating a low pressure region within the electronic device; measuring the moisture level within the sampled gas; measuring the pressure of the sampled gas; and generating a moisture level output by modifying the measured moisture level using information from the measured pressure of the gas.

X11. A method, comprising: sampling gas from within an electronic device by generating a low pressure region within a port of the electronic device; detecting the moisture level within the sampled gas; sampling ambient air from outside the electronic device; detecting the moisture level within the sampled ambient air; and calculating the moisture level within the sampled gas using the detected moisture level within the sampled gas, and the detected moisture level within the sampled ambient air.

X12. A moisture sensing apparatus, for example, an apparatus for determining the presence of water for determining moisture levels in portable electronic devices that have been subjected or suspected of coming in contact with deleterious wetting agents comprising: a room ambient moisture sensor means; a device under test (DUT) moisture sensor means; an evacuation pump means; a pneumatic solenoid means; a vacuum pressure sensor means; a standardized sampling port means; a standardized restrictor for sampling room ambient air; a standardized exhaust port for sampled air; a character display means; a LED bar graph display means; a microprocessor controlled system to automatically control and calculate moisture levels; a rechargeable DC battery powered means; an AC powered means; and a printer means.

Yet other embodiments include the features described in any of the previous statements X1, X2, X3, X4, X5, X6, X7, X8, X9, X10, X11, and X12, as combined with
  (i) one or more of the previous statements X1, X2, X3, X4, X5, X6, X7, X8, X9, X10, X11, and X12,
  (ii) one or more of the following aspects, or
  (iii) one or more of the previous statements X1, X2, X3, X4, X5, X6, X7, X8, X9, X10, X11, and X12 and one or more of the following aspects:

Means for moving gas from an electronic device to a moisture sensor.

Means for detecting moisture in gas from an electronic device.

Means for detecting moisture in the ambient air.

Means for modifying information related to the moisture in a gas from an electronic device obtained by a moisture sensor.

Means for modifying information related to the moisture in a gas from an electronic device with information related to the moisture in the ambient air.

Means for displaying information about the moisture in a gas from an electronic device.

Means for displaying information about the moisture in the ambient air.

Means for measuring the flow of a gas from an electronic device and/or ambient air past one or more moisture sensors.

Means for selecting the flow of a gas from an electronic device or ambient air to one or more moisture sensors.

Means for calibrating a device for measuring the moisture in a gas from an electronic device.

A low pressure source connected to the one or more moisture sensors and adapted to decrease pressure within the connector, and move gas from the connector to the one or more moisture sensors.

Wherein the low pressure source is one or more pumps.

A display connected to the one or more moisture sensors, the display displaying information related to the presence of moisture within the electronic device after the connector has been connected to a port of the electronic device.

Wherein the display displays information related to the relative humidity within the electronic device.

A flow sensor adapted to detect the flow of gas near the one or more moisture sensors, wherein the information related to the presence of moisture within the gas is modified with information related to the flow of gas near the one or more moisture sensors.

The information related to the flow of gas near the one or more moisture sensors is information related to the pressure of the gas.

An ambient air port connected to the one or more moisture sensors, wherein the one or more moisture sensors receive air from the ambient air port and determine the presence of moisture within the ambient air.

Wherein information related to the presence of moisture within the gas is modified with information related to the presence of moisture within the ambient air.

A valve to selectively connect the connector and the ambient air port to the one or more moisture sensors.

A first moisture sensor connected to the connector; a second moisture sensor connected to the ambient air port; and a valve to selectively connect the first and second moisture sensors to a low pressure source.

A low pressure source connected to the one or more moisture sensors and adapted to decrease pressure within the connector, decrease pressure within the electronic device, and move gas from the connector to the one or more moisture sensors.

Wherein the moisture detector includes a calibration cycle that actuates prior to receiving gas from the electronic device.

Wherein the moisture detector includes a calibration cycle that actuates after receiving gas from the electronic device.

Wherein the calibration cycle utilizes information related to the presence of moisture within the ambient air.

Wherein connecting includes pneumatically connecting the moisture detector and the interior of the electronic device.

Wherein detecting includes moving gas from the electronic device to the one or more moisture sensors.

Wherein moving gas is by a pneumatic pump.

Detecting the flow of gas near the one or more moisture sensors.

Wherein detecting the flow of gas includes detecting the pressure of the gas near the one or more moisture sensors.

Decreasing pressure at the external port of an electronic device.

Determining the moisture level within the electronic device with the one or more moisture sensors.

Determining the relative humidity within the electronic device with the one or more moisture sensors.

Determining whether the moisture within the electronic device exceeds a threshold.

Displaying information related to the moisture within the electronic device.

Displaying information related to the moisture in the gas from the electronic device.

Displaying information related to the modified moisture level.

Computing a moisture level within the electronic device using information obtained from detecting moisture within the electronic device and detecting the flow of gas.

Sampling ambient air

Detecting moisture within the ambient air.

Sampling ambient air from outside the electronic device.

Detecting the moisture level within the ambient air.

Wherein detecting moisture within the electronic device and detecting moisture within the ambient air are performed by a single moisture detector.

Facilitating detecting moisture within the ambient air while inhibiting detecting moisture within the electronic device.

Facilitating detecting moisture within the electronic device while inhibiting detecting moisture within the ambient air.

Facilitating detecting moisture within the ambient air while inhibiting detecting moisture within the electronic device; and facilitating detecting moisture within the electronic device while inhibiting detecting moisture within the ambient air; wherein the two acts of facilitating are performed at different times.

Wherein detecting moisture within the ambient air and detecting moisture within the electronic device occur simultaneously.

Calibrating the one or more moisture sensors using information related to the moisture within the ambient air obtained from detecting moisture within the ambient air.

Modifying said displaying with information related to the moisture in the ambient air.

Modifying said displaying with information related to the flow of gas over the one or more moisture sensors.

Calibrating the output from one or more moisture sensors.

Wherein calibrating is performed prior to detecting.

Wherein calibrating is performed after detecting.

Wherein generating a modified moisture level output includes modifying the measured moisture level using the detected level of moisture in the ambient air.

Connecting a moisture sensor to an external port of the electronic device.

Generating a low pressure region within the moisture sensor.

Detecting the pressure of the gas within the moisture sensor.

Wherein calculating includes using the detected pressure of the gas.

Displaying the calculated moisture level.

A low pressure source connected to the one or more moisture sensors and adapted to move gas from the connector to the one or more moisture sensors.

A flow sensor adapted to detect the flow of gas near the one or more moisture sensors.

The moisture level within the electronic device is calculated using information related to the presence of moisture within the gas, information related to the presence of moisture within the ambient air, and/or information related to the flow of gas near the one or more moisture sensors.

The flow sensor is a pressure sensor.

The information related to the flow of gas near the one or more moisture sensors is information related to the pressure of the gas.

An ambient air port connected to the one or more moisture sensors.

One or more moisture sensors receive air from the ambient air port and determine the presence of moisture within the ambient air.

A valve that selectively connects the connector and the ambient air port to the one or more moisture sensors.

The information related to the flow of air near the one or more moisture sensors is information related to the pressure of the air.

Moving gas from the electronic device to the one or more moisture sensors.

Detecting the pressure of the gas near the one or more moisture sensors.

Computing a moisture level within the electronic device.

Computing a moisture level within the electronic device using information obtained from determining the moisture level within the electronic device and/or detecting the flow of gas.

Computing a moisture level within the electronic device using information obtained from detecting moisture within the electronic device and/or detecting moisture within the ambient air.

Facilitating detecting moisture within the ambient air while inhibiting detecting moisture within the electronic device during a first time interval; and facilitating detecting moisture within the electronic device while inhibiting detecting moisture within the ambient air during a second time interval different from the first time interval.

Wherein computing a moisture level includes using information obtained from detecting the flow of gas.

Displaying the computed moisture level.

Measuring the moisture level within the sampled ambient air.

Wherein generating a moisture level output includes modifying the measured moisture level using information from the measured moisture level of the ambient air.

Displaying information related to the modified moisture level of the gas.

Detecting the pressure of the sampled gas.

Displaying the calculated moisture level to a user.

Wherein the room ambient moisture sensor is used to determine room ambient moisture levels.

Wherein the DUT moisture sensor is used to determine moisture level in a portable electronic device.

Wherein the evacuation pump is used to pull air from room ambient air.

Wherein the pneumatic solenoid is a 3-way pneumatic solenoid used to pneumatically switch out pneumatic sampling circuits.

Wherein the vacuum pressure sensor is used to determine vacuum pressure for mathematical scaling purposes.

Wherein the evacuation pump is used to pull air from inside a portable electronic device.

Wherein the standardized sampling port is used to interface with the headphone jack of portable electronic devices to permit air sampling to occur.

Wherein the standardized restrictor is used to pneumatically mimic the standardized sampling port for exact correction factor calculations.

Wherein the evacuation pump is used to pull air from inside a portable electronic device.

Wherein the character display is used to display the moisture levels of ambient air and the air sampled in a portable electronic device.

Wherein the LED bar graph is used to graphically display the relative difference of room ambient moisture and portable electronic device moisture from air sampled inside a portable electronic device.

Wherein the microcontroller is used to control electronic functionality.

Wherein the microcontroller is used to compute room ambient and device under test moisture levels.

Wherein the microcontroller is used to compute scaling factors for moisture levels in portable electronic devices due to mass transport evaporation.

Wherein the rechargeable battery operated means is used to make apparatus portable.

Wherein the AC powered means is used to make apparatus rechargeable and longer lasting.

Wherein the printer means is used to provide the user with a printed moisture level record.

Wherein standardized exhaust port is located diametrically opposite and a minimum of 3 inches from that of the DUT or ambient air sampling port.

Wherein the microprocessor automatically samples moisture sensors and computes a correction factor during active (airflow) conditions.

Reference systems that may be used herein can refer generally to various directions (for example, upper, lower, forward and rearward), which are merely offered to assist the reader in understanding the various embodiments of the disclosure and are not to be interpreted as limiting. Other reference systems may be used to describe various embodiments.

While examples, one or more representative embodiments and specific forms of the disclosure have been illustrated and described in detail in the drawings and foregoing description, the same is to be considered as illustrative and not restrictive or limiting. The description of particular features in one embodiment does not imply that those particular features are necessarily limited to that one embodiment. Some or all of the features of one embodiment can be used in combination with some or all of the features of other embodiments as would be understood by one of ordinary skill in the art, whether or not explicitly described as such. One or more exemplary embodiments have been shown and described, and all changes and modifications that come within the spirit of the disclosure are desired to be protected.

What is claimed is:

1. A method, comprising:
   connecting a moisture detector, with one or more moisture sensors and with a three-way pneumatic valve comprising a room ambient pneumatic sampling circuit and a device under test (DUT) pneumatic sampling circuit, to an electrical port of an electronic device;
   switching the three-way pneumatic valve between the room ambient pneumatic sampling circuit and the DUT pneumatic sampling circuit; and
   when the moisture detector is connected to the electronic device, detecting moisture within the electronic device with the one or more moisture sensors by switching the three-way pneumatic valve such that the moisture flows through the DUT pneumatic sampling circuit and such that the moisture is blocked from flowing through the room ambient sampling circuit.

2. The method of claim 1, wherein said connecting includes pneumatically connecting the moisture detector and the interior of the electronic device, the method comprising:
   moving gas from the electronic device to the one or more moisture sensors.

3. The method of claim 2, comprising:
   detecting the flow of gas near the one or more moisture sensors.

4. The method of claim 3, wherein said detecting the flow of gas includes detecting the pressure of the gas near the one or more moisture sensors.

5. The method of claim 3, wherein said detecting moisture within the electronic device includes determining the moisture level within the electronic device with the one or more moisture sensors.

6. The method of claim 5, comprising:
   computing a moisture level within the electronic device using information obtained from said determining the moisture level within the electronic device, and
   said detecting the flow of gas.

7. The method of claim 1, comprising:
   sampling ambient air by switching the three-way pneumatic valve such that the sampled ambient air flows through the room ambient sampling circuit and such that the sampled ambient air is blocked from flowing through the DUT pneumatic sampling circuit; and
   detecting moisture within the ambient air.

8. The method of claim 7, wherein said detecting moisture within the electronic device and said detecting moisture within the ambient air are performed by a single moisture detector.

9. The method of claim 8, comprising
   facilitating said detecting moisture within the ambient air while inhibiting said detecting moisture within the electronic device during a first time interval; and
   facilitating said detecting moisture within the electronic device while inhibiting said detecting moisture within the ambient air during a second time interval different from the first time interval.

10. The method of claim 7, comprising:
    computing a moisture level within the electronic device using information obtained from
        said detecting moisture within the electronic device, and
        said detecting moisture within the ambient air.

11. The method of claim 10, comprising:
    moving gas from the electronic device to the one or more moisture sensors; and
    detecting the flow of gas near the one or more moisture sensors;
    wherein said computing a moisture level includes using information obtained from said detecting the flow of gas.

12. The method of claim 11, comprising:
    displaying the computed moisture level.

13. The method of claim 1, wherein the electrical port is configured to electrically connect with an external electrical device, and wherein the electrical port is selected from the group consisting of a power port, a data connector, and a headphone jack.

14. The method of claim 13, wherein the electrical device is selected from the group consisting of cell phones, digital music players, watches, pagers, cameras, and tablet computers.

15. A method, comprising:
    connecting at least one device comprising: a three-way pneumatic valve comprising a room ambient pneumatic sampling circuit and a device under test (DUT) pneumatic sampling circuit, a moisture sensor and a pressure sensor to an electrical port of an electronic device;
    sampling gas from within an electronic device by generating a low pressure region within the electronic device and by switching the three-way pneumatic valve such that the sampled gas flows through the DUT pneumatic sampling circuit and such that the sampled gas is blocked from flowing through the room ambient sampling circuit;
    measuring the moisture level within the sampled gas with the moisture sensor;
    measuring the pressure of the sampled gas with the pressure sensor; and generating a moisture level output by modifying the measured moisture level using information from the measured pressure of the gas.

16. The method of claim 15, comprising:

sampling ambient air from outside the electronic device by switching the three-way pneumatic valve such that the sampled ambient air flows through the room ambient sampling circuit and such that the sampled ambient air is blocked from flowing through the DUT pneumatic sampling circuit; and measuring the moisture level within the sampled ambient air;

wherein said generating a moisture level output includes modifying the measured moisture level using information from the measured moisture level of the ambient air.

17. The method of claim 16, comprising:

displaying information related to the modified moisture level of the gas.

18. The method of claim 15, wherein the electrical port is selected from the group consisting of a power port, a data connector, and a headphone jack.

19. The method of claim 18, wherein the electrical device is selected from the group consisting of cell phones, digital music players, watches, pagers, cameras, and tablet computers.

20. A method, comprising:

connecting at least one device comprising a three-way pneumatic valve comprising a room ambient pneumatic sampling circuit and a device under test (DUT) pneumatic sampling circuit to an electronic device;

sampling gas from within the electronic device by generating a low pressure region within an electrical port of the electronic device and by switching the three-way pneumatic valve such that the sampled gas flows through the DUT pneumatic sampling circuit and such that the sampled gas is blocked from flowing through the room ambient sampling circuit;

detecting the moisture level within the sampled gas;

sampling ambient air from outside the electronic device;

detecting the moisture level within the sampled ambient air; and calculating the moisture level within the sampled gas using
the detected moisture level within the sampled gas, and
the detected moisture level within the sampled ambient air.

21. The method of claim 20, comprising:

detecting the pressure of the sampled gas;

wherein said calculating includes using the detected pressure of the gas.

22. The method of claim 21, comprising:

displaying the calculated moisture level to a user.

23. The method of claim 20, wherein the electrical port is selected from the group consisting of a power port, a data connector, and a headphone jack.

24. The method of claim 23, wherein the electrical device is selected from the group consisting of cell phones, digital music players, watches, pagers, cameras, and tablet computers.

* * * * *